United States Patent [19]

Temple et al.

[11] Patent Number: 4,892,874

[45] Date of Patent: Jan. 9, 1990

[54] SYNERGISTIC ANTICANCER COMBINATION

[75] Inventors: Carroll G. Temple; Glynn P. Wheeler, both of Birmingham, Ala.

[73] Assignee: Southern Research Institute, Birmingham, Ala.

[21] Appl. No.: 926,559

[22] Filed: Nov. 4, 1986

[51] Int. Cl.[4] .................. A61K 31/50; A61K 31/495; A61K 31/44

[52] U.S. Cl. ..................... 514/249; 514/283

[58] Field of Search ................ 514/249, 283

[56] References Cited

U.S. PATENT DOCUMENTS 4,450,160 5/1984 Temple, Jr. et al. ............... 424/250

OTHER PUBLICATIONS

Cancer Research, Nov., 1982, vol. 42, No. 11, pp. 4382–4386.
J. Med. Chem. Mar., 1980, vol. 23, No. 3, pp. 300–304.
Wheeler et al., Cancer Res., 43, 3567 (1983).

Temple et al., J. Med. Chem., 26, 91 (1983).
1986 AACR Abstract Form.

*Primary Examiner*—Jerome D. Goldberg
*Attorney, Agent, or Firm*—Roylance, Abrams, Berdo & Goodman

[57] ABSTRACT

It is disclosed that a compound having the formula

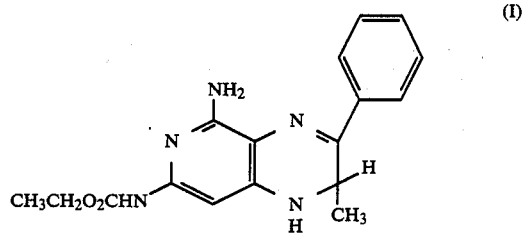

or a pharmaceutically acceptable salt thereof in combination with vincristine produces synergistic antitumor activity.

9 Claims, No Drawings

SYNERGISTIC ANTICANCER COMBINATION

BACKGROUND OF THE INVENTION

This invention relates to a synergistic anticancer combination.

The antimitotic vinca alkaloid vincristine is well known and is currently used clinically in the treatment of neoplasms. The primary effect of this agent is to prevent mitosis by interfering with the function of microtubules, which results in the accumulation of cells in metaphase. The antitumor activity of vincristine against lymphocytic leukemia P388 has been reported by Wheeler et al, Cancer Res., 42, 791 (1982). These experiments were performed by the protocols of the National Cancer Institute, National Institutes of Health as described by Geran et al, J. Cancer Chemother. Rep., 3 (2), 1972. As a clinical agent, vincristine is effective in the treatment of a number of tumors, e.g., leukemias, lymphomas, chloriocarcinoma, Wilm's tumor, neuroblastoma, rhabdomyosarcoma and carcinoma of the testis, and less effective in the treatment of solid tumors, e.g., breast and lung tumors, see Stearn in "The Catharanthus Alkaloids, Botany, Chemistry, Pharmacology and Clinical Uses", Taylor and Farnsworth, eds, Marcel Dekker, Inc., New York, 1973, p. 237.

U.S. Pat. No. 4,450,160 to Temple et al discloses that the compound having the formula:

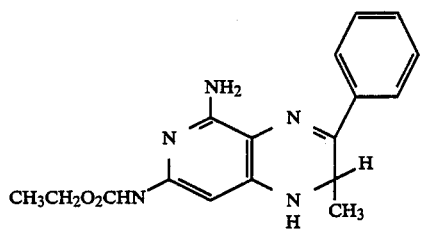

possesses anticancer activity. This compound is one of a series of 1,2-dihydropyrido[3,4-b]pyrazines that have been reported to have antitumor activity against lymphocytic leukemia P388 in mice by Wheeler et al, Cancer Res., 43, 3567 (1983) and Temple et al, J. Med. Chem., 26, 91 (1983). The National Cancer Institute has assigned two National Service Center (NSC) numbers to salts of the compound of Formula I, i.e., NSC 350386 designates the hydrochloride (HCl) salt and NSC 370147 designates the 2-hydroxyethyl sulfonate ($HOCH_2CH_2SO_3H$) salt.

Wheeler et al in Cancer Research, 43, pages 3567–3575, Aug., 1983, discloses the synergistic cytotoxicity of a combination of vincristine and a compound having the formula:

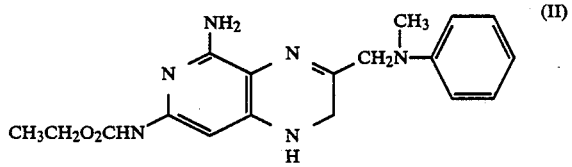

SUMMARY OF THE INVENTION

It has now been found that a compound of Formula I or a pharmaceutically acceptable salt thereof in combination with vincristine produces synergistic antitumor (antineoplastic) activity. Such pharmaceutically acceptable salts include the hydrochloride and the 2-hydroxyethyl sulfonate. Thus, in accordance with the practice of this invention, there is administered to a mammal, including man, afflicted with a tumor or neoplasm a synergistic combination of an antineoplastically effective amount of a compound of Formula I or a pharmaceutically acceptable salt thereof and an antineoplastically effective amount of vincristine. The two components of the synergistic combination may be administered to the mammal separately or in admixture. Preferably, from about 0.3 to about 4.6 to parts by weight of vincristine are administered to the mammal per 1.0 part by weight of the compound of Formula I or a pharmaceutically acceptable salt thereof and these components are administered in a total amount ranging from about 1 to about 35 mg per kg of body weight per day.

By the term "tumor" or "neoplasm" is meant any new and abnormal cell growth, specifically a new growth of tissue which is uncontrolled and progressive. The synergistic combination of this invention may be used, for example, in the treatment of leukemia, Hodgkin's disease, lymphosarcoma, reticulum-cell sarcoma, rhabdomyosarcoma, neuroblastoma, and Wilm's tumor.

DETAILED DESCRIPTION OF THE INVENTION

The treatment of CD2F1 mice implanted with leukemia P388 cells with a combination of a salt of the compound of Formula I and vincristine results in a synergistic decrease in tumor cell population based on an increase in life span. The synergistic combination may be administered parenterally or intraperitoneally on a daily or other basis. The dosage regimen may be adjusted to provide the optimum therapeutic response.

Solutions of the components of the synergistic combination can be prepared in water suitably mixed with a surfactant such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms. The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol), suitable mixtures thereof and vegetable oils. The proper fluidity can be maintained, for example, by the use of a coating such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred method of preparation are vacuum drying and the freeze-drying technique which yield a powder of the active ingredients plus any additional desired ingredient from a previously sterile-filtered solution thereof.

Several studies were carried out to determine the potential for therapeutic synergy with vincristine and the compound of Formula I, or a pharmaceutically acceptable salt thereof. In these studies, the tumor model selected was P388 murine leukemia because of its demonstrated high predictability for clinical efficacy against a broad spectrum of human tumors (see, for example, Vendetti, "Relevance of Transplantable Animal-Tumor Systems to the Selection of New Agents for Clincal Trial", *Pharmacological Basis of Cancer Chemotherapy*, The Williams & Wilkins Company, 1975, pps. 245-270; and Simpson-Herren et al, "Evaluation of In Vivo Tumor Models for Predicting Clinical Activity for Anticancer Drugs, *Proc. Am. Assoc. Cancer Res.*, 26:330 (1985). In these studies, synergism was considered to have been demonstrated if the combination of vincristine and the compound of Formula I produced a greater reduction in tumor cell population than the additive changes in tumor cell populations with the compound of Formula I and vincristine individually.

The following examples illustrate the invention. In these examples, both the cancer cells and the drugs were administered intraperitoneally. In Example 2, the compound of Formula I and vincristine were administered substantially simultaneously, i.e., within about a minute of each other, in saline. In Tables I, II and III, "% ILS" refers to percentage of increase in life span and "$Log_{10}$ Change" means the net log change in viable tumor cell population at the end of treatment as compared to the start of treatment; e.g., a $-6$ log change means a 99.999% reduction and a $+3$ log change means that there was a 1000-fold increase in tumor burden at the end of treatment.

EXAMPLE 1

Table I sets forth biological data for vincristine (VCR), for the hydrochloride salt of the compound of Formula I (350386) and for the 2-hydroxyethyl sulfonate salt of the compound of Formula I (370147). This Table reports the results of experiments to determine the responses of the sensitive leukemia P388 (P388/0) and the vincristine resistant leukemia P388 (P388/VCR) to the compound of Formula I and vincristine. At the indicated doses on days 1,5,9, vincristine gave a higher increase in life span and a higher decrease in tumor cell population against P388/0 than against P388/VCR. The degree of resistance of P388/VCR to vincristine is indicated by the difference in tumor cell populations between P388/0 and P388/VCR. The compound of Formula I was tested on two different schedules, days 1-5 and day 1 only, against P388/0 and P388/VCR. The results set forth in Table I indicate that both P388/0 and P388/VCR respond to the compound of Formula I, but a slight cross resistance to the compound of Formula I was shown on the days 1-5 schedule.

TABLE I

Sensitivity of Vincristine-Resistant P388 Leukemia to NSC 350386 and NSC 370147

| Drug | Dose (mg/kg/dose) | Schedule (days) | P388/0; $10^6$ Cell Implant Median % ILS | P388/0; $10^6$ Cell Implant $Log_{10}$ Change | P388/VCR; $10^6$ Cell Implant Median % ILS | P388/VCR; $10^6$ Cell Implant $Log_{10}$ Change | Difference |
|---|---|---|---|---|---|---|---|
| VCR | 2.0 | 1,5,9 | | | Toxic | | |
| | 1.5 | | | | +60 | +1.3 | |
| | 1.0 | | | | +45 | +1.6 | |
| 350386 | 2.0 | qd 1-5 | | | Toxic | | |
| | 1.0 | | | | Toxic | | |
| | 0.5 | | | | +70 | −2.0 | |
| VCR | 2.5 | 1,5,9 | +160 | −5.4 | +27 | +1.4 | 6.8 |
| | 2.0 | | +140 | −4.0 | +31 | +1.4 | 5.4 |
| | 1.5 | | +140 | −4.0 | +27 | +1.4 | 5.4 |
| | 1.0 | | +115 | −2.4 | +27 | +1.4 | 3.8 |
| 370147 | 1.0 | qd 1-5 | +85 | −3.0 | Toxic | | |
| | 0.75 | | +70 | −2.0 | +45 | −1.0 | 1.0 |
| | 0.50 | | +50 | −0.7 | +40 | −0.5 | 0.2 |
| | 0.33 | | +30 | +0.7 | +27 | +1.0 | 0.3 |
| 370147 | 10.0 | Day 1 only | Toxic | | Toxic | | |
| | 7.5 | | +70 | −4.7 | +36 | −4.2 | 0.5 |
| | 5.0 | | +40 | −2.7 | +18 | −2.1 | 0.6 |

EXAMPLE 2

Tables II and III set forth biological data for vincristine (VCR) and for the 2-hydroxyethyl sulfonate salt of the compound of Formula I (370147), both by themselves and in combination administered separately. The response of a $10^6$ cell inoculun of leukemia P388/0 in mice to treatment with combinations of the compound of Formula I and vincristine are listed in Table II. Although a greater response, relative to controls, was obtained at a dose ratio (I:vincristine) of 1:1 and 2:1, the tumor was not sufficiently advanced in the combinations containing 2 mg of vincristine to demonstrate a therapeutic advantage. The activities of combinations of the compound of Formula I and vincristine administered to mice with a $10^7$ cell inoculun of leukemia P388/0 are listed in Table III. In the control experiments, the maximum effect of vincristine alone was a reduction of the tumor cell population by two and one half orders of magnitude, whereas, the compound of Formula I alone produced a slight increase in tumor cell population. The experiments with combinations of the compound of Formula I and vincristine produced a greater reduction in tumor cell population than the additive changes in tumor cell populations with the compound of Formula I and vincristine individually which indicates that combinations of the compound of Formula I and vincristine are therapeutically synergistic.

TABLE II

Response of P388 Leukemia, $10^6$ Cell Implant, to Vincristine Plus NSC 370147

| Drug | Dose (mg/kg/dose) | Schedule (days) | Median % ILS | Log$_{10}$ Change | Survivors |
|---|---|---|---|---|---|
| VCR | 2.0 | 1,5,9 | +163 | −6.7 | 1/10 |
| | 1.5 | | +136 | −4.8 | |
| | 1.0 | | +118 | −3.4 | |
| 370147 | 2.25 | 1,5,9 (LD$_{20}$) | +100 | −2.1 | |
| | 1.5 | | +81 | −0.7 | |
| | 1.0 | | +40 | +1.5 | |
| | 0.67 | | +27 | +1.7 | |
| | 0.44 | | +22 | +1.8 | |
| VCR + 370147 | 2.0 + 0.67 | 1,5,9 | +177 | −6.7 | |
| VCR + 370147 | 2.0 + 0.44 | 1,5,9 | +150 | −5.8 | 2/10 |
| VCR + 370147 | 1.0 + 1.0 | 1,5,9 | +145 | −5.5 | |
| VCR + 370147 | 0.5 + 1.0 | 1,5,9 | +127 | −4.1 | |

TABLE III

Response of P388 Leukemia, $10^7$ Cell Implant, to Vincristine Plus NSC 370147

| Drug | Dose (mg/kg/dose) | Schedule (days) | Median % ILS | Log$_{10}$ Change | Survivors |
|---|---|---|---|---|---|
| VCR | 2.0 | 1,5,9 | +133 | −2.5 | |
| | 1.5 | | +122 | −1.8 | |
| | 1.0 | | +100 | −0.6 | |
| 370147 | 2.25 | 1,5,9 | +77 | +0.4 | |
| | 1.5 | | +72 | +0.5 | |
| | 1.0 | | +11 | +1.3 | |
| | 0.67 | | +11 | +1.3 | |
| VCR + 370147 | 2.0 + 1.0 | 1,5,9 | +177 | −4.9 | 2/10 |
| VCR + 370147 | 1.5 + 1.5 | 1,5,9 | +177 | −4.9 | |
| VCR + 370147 | 1.0 + 1.0 | 1,5,9 | +144 | −3.1 | |
| VCR + 370147 | 0.5 + 1.5 | 1,5,9 | +150 | −3.4 | |

What is claimed is:

1. A method for the treatment of a mammal afflicted with a tumor comprising administering to said mammal a synergistic combination of an antineoplastically effective amount of a compound having the formula

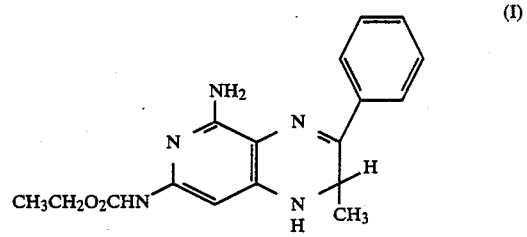

or a pharmaceutically acceptable salt thereof and an antineoplastically effective amount of vincristine.

2. A method as defined in claim 1 wherein the two components of the synergistic combination are administered to said mammal separately.

3. A method as defined in claim 1 wherein from about 0.3 to about 4.6 parts of vincristine are administered to said mammal per 1.0 part of the compound of Formula I or a pharmaceutically acceptable salt thereof.

4. A method as defined in claim 1 wherein said synergistic combination is administered to said mammal in an amount ranging from about 1 to about 3 mg per kg of body weight per day.

5. A method as defined in claim 3 wherein said synergistic combination is administered to said mammal in an amount ranging from about 1 to about 3 mg per kg of body weight per day.

6. A method as defined in claim 1 wherein said synergistic combination comprises the 2-hydroxyethyl sulfonate salt of the compound of Formula I and vincristine.

7. A method as defined in claim 3 wherein said synergistic combination comprises the 2-hydroxyethyl sulfonate salt of the compound of Formula I and vincristine.

8. A method as defined in claim 4 wherein said synergistic combination comprises the 2-hydroxyethyl sulfonate salt of the compound of Formula I and vincristine.

9. A method as defined in claim 5 wherein said synergistic combination comprises the 2-hydroxyethyl sulfonate salt of the compound of Formula I and vincristine.

* * * * *